(12) United States Patent
Martins et al.

(10) Patent No.: US 11,844,721 B2
(45) Date of Patent: Dec. 19, 2023

(54) CRYOCABIN ARRANGEMENT AND AN OPERATING METHOD

(71) Applicant: CRYOTECH NORDIC AS, Väana (EE)

(72) Inventors: Jean-Patrick Enzio Martins, Tallinn (EE); Juha Yliollitervo, Järvenpää (FI)

(73) Assignee: CRYOTECH NORDIC AS, Väana (EE)

( * ) Notice: Subject to any disclaimer, the term of this patent is extended or adjusted under 35 U.S.C. 154(b) by 0 days.

(21) Appl. No.: 17/623,212

(22) PCT Filed: Jun. 24, 2020

(86) PCT No.: PCT/EP2020/067609
§ 371 (c)(1),
(2) Date: Dec. 27, 2021

(87) PCT Pub. No.: WO2020/260347
PCT Pub. Date: Dec. 30, 2020

(65) Prior Publication Data
US 2022/0347007 A1    Nov. 3, 2022

(30) Foreign Application Priority Data
Jun. 25, 2019 (FI) .................................. 20195561

(51) Int. Cl.
*A61F 7/00* (2006.01)

(52) U.S. Cl.
CPC .... *A61F 7/0053* (2013.01); *A61F 2007/0057* (2013.01); *A61F 2007/0096* (2013.01)

(58) Field of Classification Search
CPC .. A61F 7/00; A61F 7/0053; A61F 2007/0054; A61F 2007/0056;
(Continued)

(56) References Cited

U.S. PATENT DOCUMENTS

| 4,838,270 A | 6/1989 | Donnerhack et al. |
| 7,244,269 B2 * | 7/2007 | Brojek ................. A61F 7/0053 |
| | | 607/104 |

(Continued)

FOREIGN PATENT DOCUMENTS

| CN | 109157323 | 1/2019 |
| EP | 3 195 834 | 7/2017 |

(Continued)

OTHER PUBLICATIONS

International Search Report for PCT/EP2020/067609 dated Sep. 25, 2020, 5 pages.

(Continued)

*Primary Examiner* — Ahmed M Farah
(74) *Attorney, Agent, or Firm* — NIXON & VANDERHYE

(57) ABSTRACT

The invention pertains to a method for operating a cryocabin arrangement 100 with an open-top cabin 10, a cooling unit 20 and a number of fluid circulation units 30. The method comprises receiving user-specific data comprising at least temperature indications measureable, by a number of sensor devices, at skin surface of the user upon delivery of cooling fluid 201 into the cabin via the cooling unit followed by intake and recirculation of said cooling fluid by fluid circulation units, which further return recirculated cooling fluid 301 inside said cabin, and based on said user-specific data, selectively adjusting distribution of said cooling fluid 201, 301 inside the cabin, in terms of at least speed and/or direction of a fluidic flow, to a predetermined level during an operation cycle.

20 Claims, 8 Drawing Sheets

(58) Field of Classification Search
CPC ...... A61F 2007/0057; A61F 2007/0063; A61F 2007/0069; A61F 7/0058; A61F 2007/0095; A61F 2007/0096
USPC .............................................. 607/81, 85–87
See application file for complete search history.

(56) References Cited

U.S. PATENT DOCUMENTS

| | | | |
|---|---|---|---|
| 8,162,930 B2* | 4/2012 | Brojek | A61F 7/0053 606/22 |
| 2012/0179230 A1* | 7/2012 | Ramirez Barrones | A61F 7/02 607/104 |
| 2013/0025302 A1 | 1/2013 | Lyubchenko | |
| 2015/0018903 A1* | 1/2015 | Vapaavalta | A61H 33/00 607/104 |
| 2017/0209302 A1* | 7/2017 | Yliollitervo | F25D 3/10 |
| 2017/0326042 A1 | 11/2017 | Zeng et al. | |
| 2019/0151140 A1* | 5/2019 | Trembley | G16H 20/40 |
| 2019/0216637 A1* | 7/2019 | Sierra Murillo | A61G 10/02 |

FOREIGN PATENT DOCUMENTS

| | | | | |
|---|---|---|---|---|
| EP | 3195834 A1 * | 7/2017 | | A61F 7/0053 |
| RU | 2 635 770 | 11/2017 | | |

OTHER PUBLICATIONS

Written Opinion of the ISA for PCT/EP2020/067609 dated Sep. 25, 2020, 7 pages.
Search Report for FI20195561, dated Feb. 5, 2020, 2 pages.

* cited by examiner

CRYOCABIN ARRANGEMENT AND AN OPERATING METHOD

CROSS-REFERENCE TO RELATED APPLICATIONS

This application is the U.S. national phase of International Application No. PCT/EP2020/067609 filed Jun. 24, 2020 which designated the U.S. and claims priority to Finnish Patent Application No. 20195561 filed Jun. 25, 2019, the entire contents of each of which are hereby incorporated by reference.

FIELD OF THE INVENTION

The present invention generally relates to equipment for whole-body cryotherapy and methods for operating thereof. More particularly, the invention concerns a whole-body cryocabin arrangement and a method for operating the same, in which method delivery of cooling fluids into the cabin is controlled with high precision during an operation cycle.

BACKGROUND

Whole body cryotherapy or whole body cold therapy (WBCT) is a recognized procedure for promoting muscle recovery and for enhancing general well-being of an individual. Upon impact of air-infused cryogenic liquids, whole body cryotherapy treatment is believed to invoke and/or reactivate internal resources of the organism, thus promoting its natural capacity for a self-defense against various diseases including asthma, hormone deficiencies, joint inflammation and skin disorders, such as allergies and psoriasis. Long-term effects of cryotherapy include an enhanced immune resistance of the organism and an improved flexibility and elasticity of soft tissues and skin. Cold treatments also promote cell replacement processes naturally occurring within the body, and elimination of dead cells, accordingly.

Cryotherapy treatment aims at inducing, in the persons' skin and an underlying (soft) tissue, a thermal (cold) shock response, thereupon the aforementioned (cryo)therapeutic effect(s) take place. Thermal shock response is induced upon a sudden cold impact onto a plurality of body areas, whereby the body develops local stress responses, followed by activation of metabolic processes, acceleration and intensification of blood circulation, increased oxygen supply to blood and tissues and release of anti-inflammatory and analgesic substances, that altogether results in at least alleviation of pain, reduced swelling and diminished muscle tension. In order to achieve the thermal shock response in skin, temperature at skin surface should be dropped down to approximately zero degrees Celsius.

In conventional cryotherapy methods the patient is exposed to an impact of the extreme temperatures, such as below −100 degrees Celsius (typically within a range of −110 to −170° C.), for short time spans, typically 0.5-3 minutes at a time. In these methods, the required (cryo)therapeutic effect is achieved by using cryogenic coolants, such as (liquefied) carbon dioxide ($CO_2$) and liquid nitrogen ($LN_2$). Cryogenic coolant is blown over an entire patient's body (cryosauna) by means of compressed air or by pressure created upon evaporation and boiling of the liquid gas. An exemplary open-top device of the kind is disclosed in the U.S. patent application publication No. 2013/0025302 (Lyubchenko).

As an alternative to cryogenic liquid operable WBCT chambers, electric cryotherapy chamber solutions are available on the market. In electric cryochambers, temperature reduction is achieved without cryogenic liquid, but through the use of gaseous medium, typically air, cooled to below −100 degrees by electrically powered cooling aggregate. However, cooling power of a majority of such devices is insufficient for generating the cold-induced thermal shock response indispensable for achieving the (cryo)therapeutic effect(s). Those solutions that do produce temperatures below −100 degrees Celsius are extremely expensive. Typical electric-powered cryochamber is a closed-space chamber (not open-top) with essentially no air circulation in its' interior. In an absence of air circulation, heat exchange between the patients' skin and the ambient is markedly reduced.

One common problem associated with the devices for whole body cryotherapy known from the art (both cryogenic liquid- and electric operable) is poor adjustability of treatment parameters, such as temperature, velocity and/or direction of coolant flow, throughout the cryotherapy session. An exemplary solution disclosed in the U.S. Pat. No. 4,838,270 (Donnerhack et al) teaches adjusting the directions of cold gas flowing into the cryotherapy cabin before the treatment. Mentioned patent concerns a walk-in, open-top cabin in the form of a half-shell, in which cold gas produced by mixing dry air with liquefied nitrogen can be directed into the cabin via nozzles rotatable about their vertical axis in accordance to height and body shape of the patient.

None of the abovementioned cryoliquid- or electric cooling based solutions take into an account the fact that ability to withstand cold largely varies amongst individuals. For example, intensity of blood flow circulation in skin and underlying tissue, naturally varying amongst individuals, has a significant impact on temperature conditions at which the thermal shock response is attained at skin surface. Some individuals could not fully benefit from cryotherapy treatments due to personal cold intolerance. Additionally, some body regions are generally more cold-sensitive than the others (local sensitivity). During a standard whole body cryotherapy session, such patient is subjected to the risk of cold injury. Nonetheless, shortened or conducted at higher temperatures treatment session results in decreased treatment efficiency, since conditions required for achieving the thermal shock response on skin become more difficult to reach.

It is evident that in an absence of the thermal shock response, the treatment cannot be considered therapeutic in a sense of imposing healing and/or health-promoting effects onto an individual.

In this regard, it is still desirable to complement and update the field of technology related to equipment and methods used in whole body cold treatments and to develop new concepts for controlling coolant circulation- and/or temperature related parameters inside a cryocabin in a user-specific manner.

SUMMARY OF THE INVENTION

An objective of the present invention is to solve or at least alleviate each of the problems arising from the limitations and disadvantages of the related art. The objective is achieved by various embodiments of a whole-body cryocabin arrangement and a method for operating said arrangement. Thereby, in one aspect of the invention, a method for operating a cryocabin arrangement is provided.

In embodiment, a method is provided for operating a cryocabin arrangement comprising an open-top cabin, a cooling unit and a number of fluid circulation units, the method comprises:

receiving user-specific data comprising at least temperature indications (t1) measureable, by a number of sensor devices, at skin surface of a user upon delivery of cooling fluid into the cabin via the cooling unit followed by intake and recirculation of said cooling fluid by fluid circulation units, which further return recirculated cooling fluid inside said cabin, and based on said user-specific data, selectively adjusting, during an operation cycle, a number of variables related to distribution of said cooling fluid inside the cabin to a predetermined level, said variables being at least speed- and/or direction of a fluidic flow.

In embodiment, the fluid distribution variables (speed and/or direction vectors) are adjusted to reach the values, at which temperature indications (t1) measureable at the user skin surface are within a range of 0 to −1 degree Celsius.

In embodiment, receiving the user-specific data and adjusting distribution of cooling fluid inside the cabin are performed in real-time.

In embodiment, the cooling fluid distributed inside the cabin is adjusted to a temperature (t2) equal to or above −40 degrees Celsius (° C.).

In embodiments, the cooling fluid is air.

In embodiment, the method comprises delivery of the cooling fluid into the cabin essentially along the entire height of said cabin.

In embodiment, recirculation and return of the cooling fluid into the cabin is implemented by the fluid circulation units arranged at both sides of the cooling unit essentially opposite one another.

In embodiment, recirculated cooling fluid is returned into the cabin along a path inclined at an angle within a range of 30-50 degrees related to vertical walls of said cabin.

In embodiment, the cryocabin arrangement is electrically operated.

In embodiment, distribution of the cooling fluid inside the cabin is supplemented by delivery, preferably by spraying, of an aqueous-based solution into the cabin by a number of vaporizer devices. Said aqueous-based solution preferably comprises an aqueous component and an oil component.

In an aspect, an electrically operated cryocabin arrangement is further provided.

In embodiment, the electrically operated cryocabin arrangement comprises an open-top cabin, a cooling unit configured to deliver cooling fluid directly into the cabin, and a number of fluid circulation units, which cryocabin arrangement further comprises a data processing unit that receives user-specific data comprising at least temperature indications (t1) measureable at skin surface of the user by a number of sensor devices upon delivery of cooling fluid into the cabin via the cooling unit followed by intake and recirculation of said cooling fluid by fluid circulation units, which further return recirculated cooling fluid inside said cabin, and based on said use-specific data, selectively adjusts, in real time, distribution of said cooling fluid inside the cabin, in terms of at least speed and/or direction of a fluidic flow, to a predetermined level during an operation cycle.

In embodiment, the cryocabin arrangement further comprises a number of vaporizer devices configured to deliver, preferably by spraying, an aqueous-based solution into the cabin.

In further aspect, a composition for use in a method according to some previous aspect is provided. In embodiment, said composition is provided in the form of an aqueous-based solution and comprises an aqueous component and an oil component, wherein the aqueous component is a micellar aqueous solution and wherein the oil component is a vegetable oil selected from the group consisting of: argan oil, sunflower seed oil, olive oil, jojoba oil, avocado oil, almond oil, coconut oil, castor oil, rosehip oil, and any combination thereof.

The utility of the present invention arises from a variety of reasons depending on each particular embodiment thereof. Overall, the invention provides for operating a cryocabin such, that during an operation cycle a variety of parameters can be monitored and adjusted with high precision and taking into account personal sensitivity to cold. Said parameters include, but are not limited to source, velocity (speed rendered with a direction vector), speed and direction of fluidic stream(s) distributed inside the cabin. By enabling monitoring and personalized adjustment of coolant flow related parameters in real-time, the invention allows for generating fluidic streams entering the cabin with predetermined speed and in predetermined direction/from a predetermined source, whereby excessive cooling of cold-sensitive body areas could be effectively avoided. At the same time, the body areas less sensitive to cold could still receive adequate treatment sufficient to attain the cold-induced thermal shock response.

Thermal sensitivity varies approximately 100-fold over the body surface. Therefore, an arrangement, by which the cold-induced thermal shock response could be attained uniformly throughout the entire body of an individual (that is, at the body areas having different sensitivity to cold), is undoubtedly beneficial, in terms of both treatment efficiency and cost-effectiveness, for a person whose intention is to undergo a series of treatments by cryotherapy The invention further provides an arrangement for attaining the cold-induced thermal shock response uniformly throughout the entire body of an individual by monitoring and adjusting, in a real-time regime, delivery of cooling fluid to particular body areas.

The invention is preferably realized as an electrically cooled cabin solution, which does not require utilization of cryogenic coolants (liquid gases). The (cryo)therapeutic effect or effects stipulated by generation of said cold-induced thermal shock response is/are thus achieved for the entire body, at temperatures much higher than that utilized for conventional cryotherapy. In fact, the invention allows for attaining healing- and/or health-promoting benefits typically associated with invoking the thermal shock response by exposing the individual to extremely low temperatures (−100 degrees Celsius and lower) at the aforesaid "high" temperatures, viz. within a range of −45° C. to −15° C., in some instances, within a range of −35° C. to −25° C.

The invention allows for adjusting parameters related to cooling fluid distribution inside the cabin such, as to establish treatment conditions suitable for users with low perception threshold for cold.

The term "a user" is utilized in present disclosure to indicate a subject, such as a human or a nonhuman mammal, positioned inside the cryocabin.

The expression "a number of" refers in present disclosure to any positive integer starting from one (1), e.g. to one, two, or three. The expression "a plurality of" refers to any positive integer starting from two (2), e.g. to two, three, or four.

Different embodiments of the present invention will become apparent by consideration of the detailed description and accompanying drawings.

DETAILED DESCRIPTION OF THE EMBODIMENTS

Figure 1A:
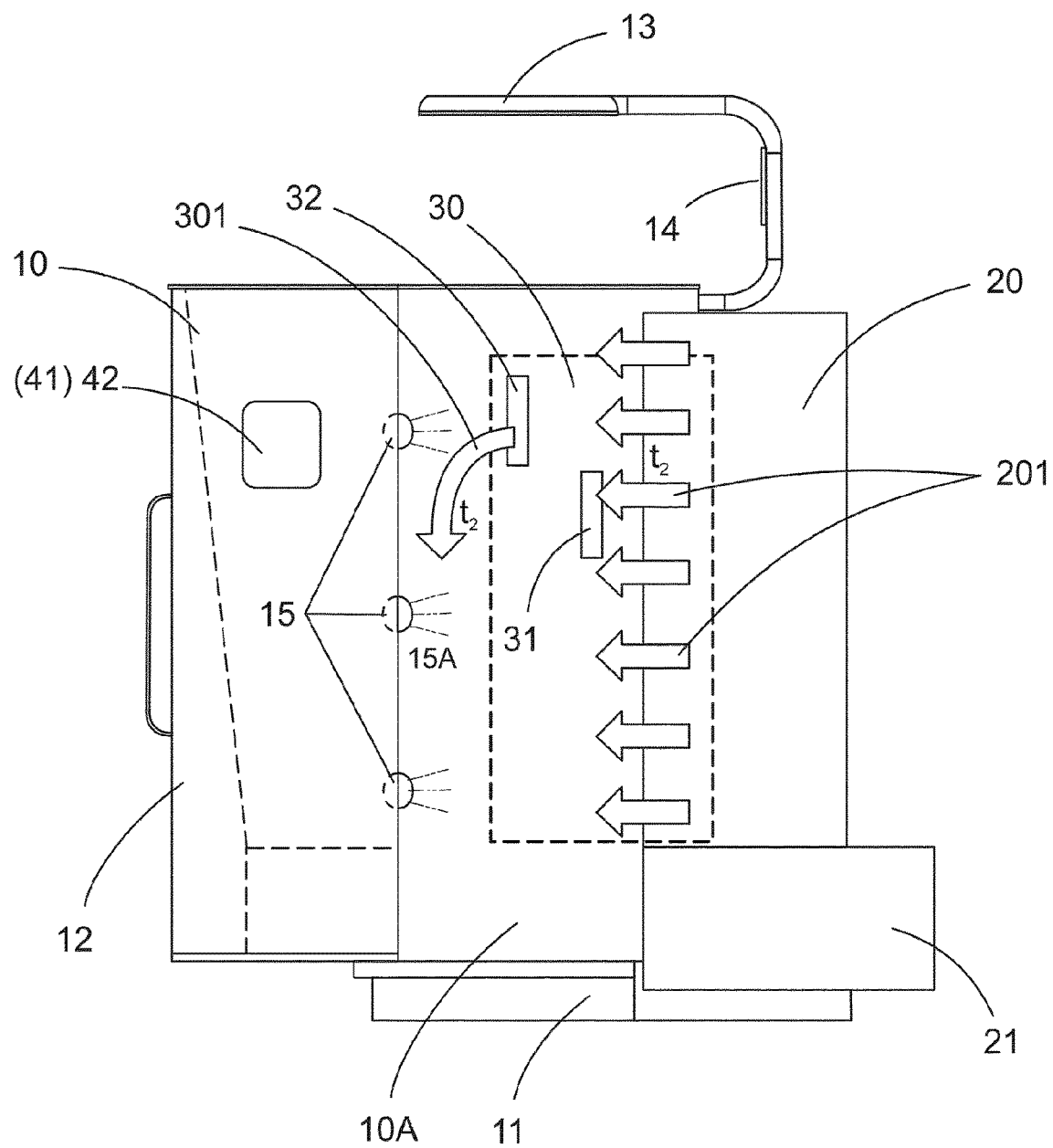
FIG. 1A schematically illustrates a cryocabin arrangement 100 operated by a method, according to an embodiment, viewed from the side.

Detailed embodiments of the present invention are disclosed herein with the reference to accompanying drawings. The same reference numerals are used throughout the drawings to refer to same members as follows:
- 100—a cryocabin arrangement;
- 101—a user;
- 10—a cabin;
- 10A—an interior of the cabin;
- 11, 11A—a base and a standing platform, accordingly;
- 12—a door;
- 13—illumination device(s);
- 14—parameter display(s);
- 15, 15A—vaporizer device(s) and a cooling solution, accordingly;
- 16—sensor device(s);
- 17—protective shields;
- 18—control device(s);
- 20—a cooling unit;
- 21—a compressor unit;
- 30 (30A, 30B)—fluid circulation unit(s);
- 31—cooling fluid intake appliance(s);
- 32—cooling fluid return appliance(s);
- 33—an impeller device;
- 41—a processing unit;
- 42—a control terminal;
- 201—a stream of cooling fluid delivered into the cabin from the cooling unit 20;
- 301 (301A, 301B)—streams of cooling fluid returned into the cabin from the fluid circulation units 30 (30A, 30B), accordingly.

Figure 1B:
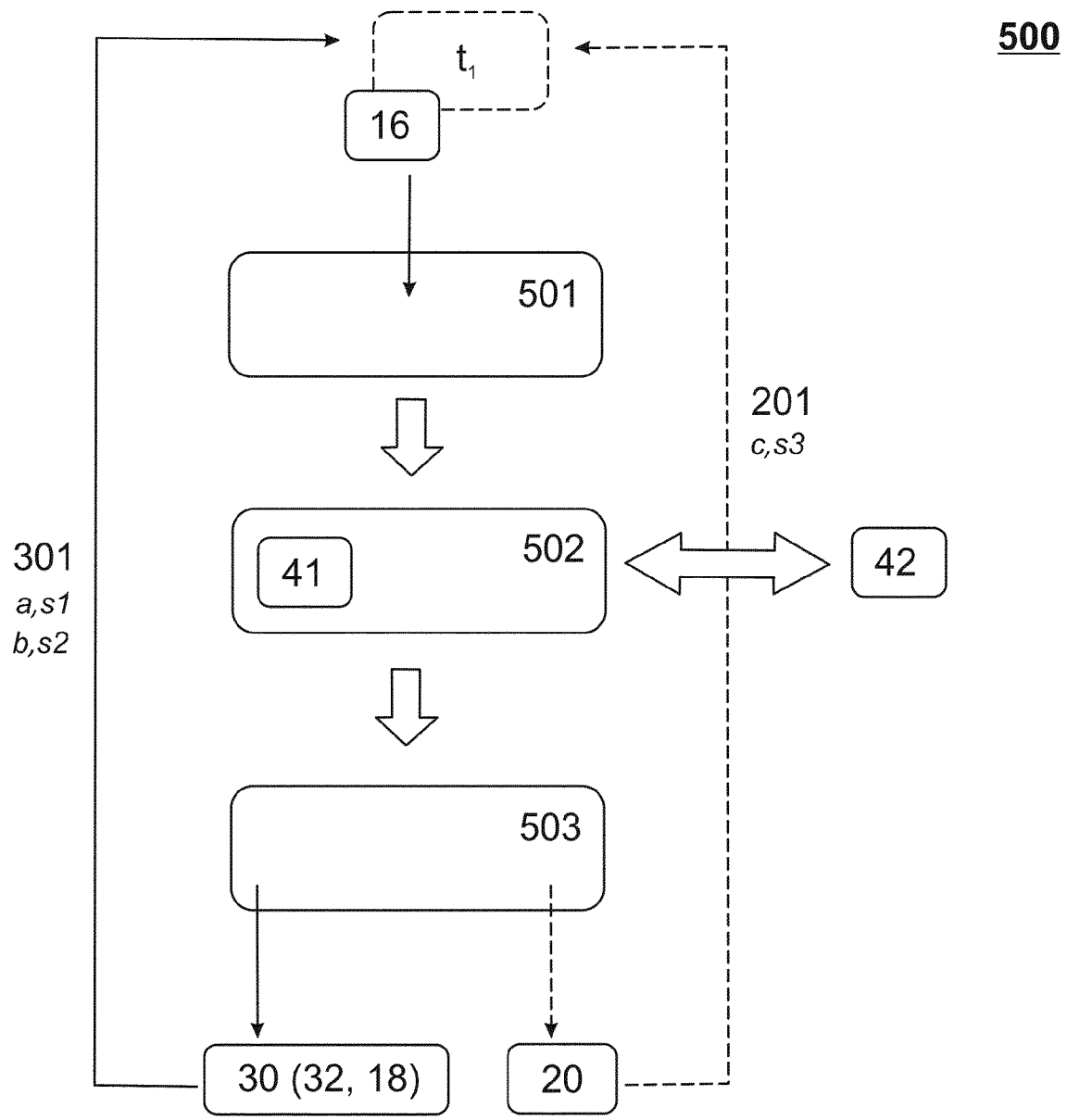
FIG. 1B schematically illustrates a method for operating the cryocabin arrangement, according to the embodiments.
Figure 2A:
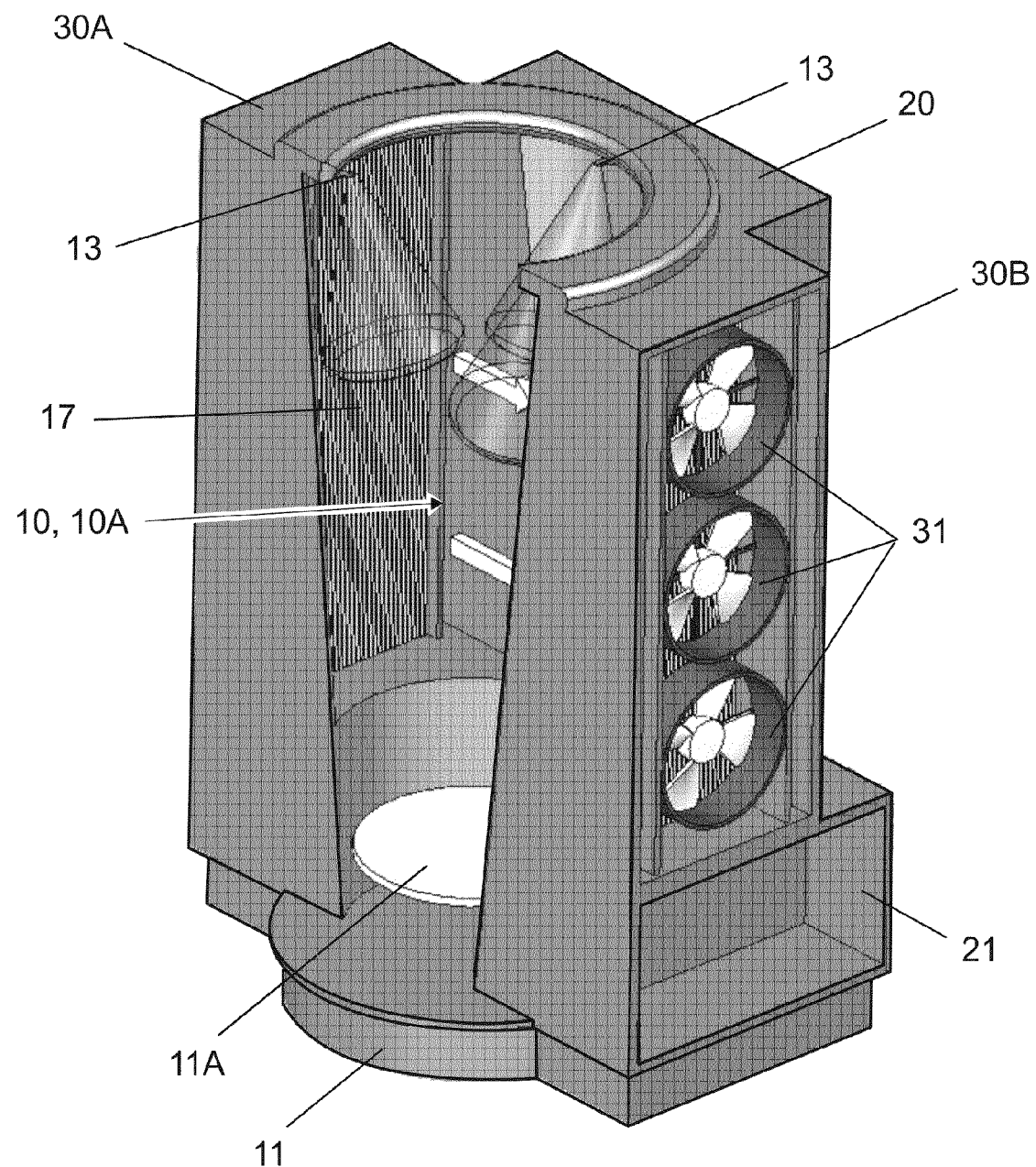
FIGS. 2A and 2B are a prospective view and a front view, accordingly of the cryocabin arrangement 100 operated by a method, according to the embodiments.
Figure 2B:
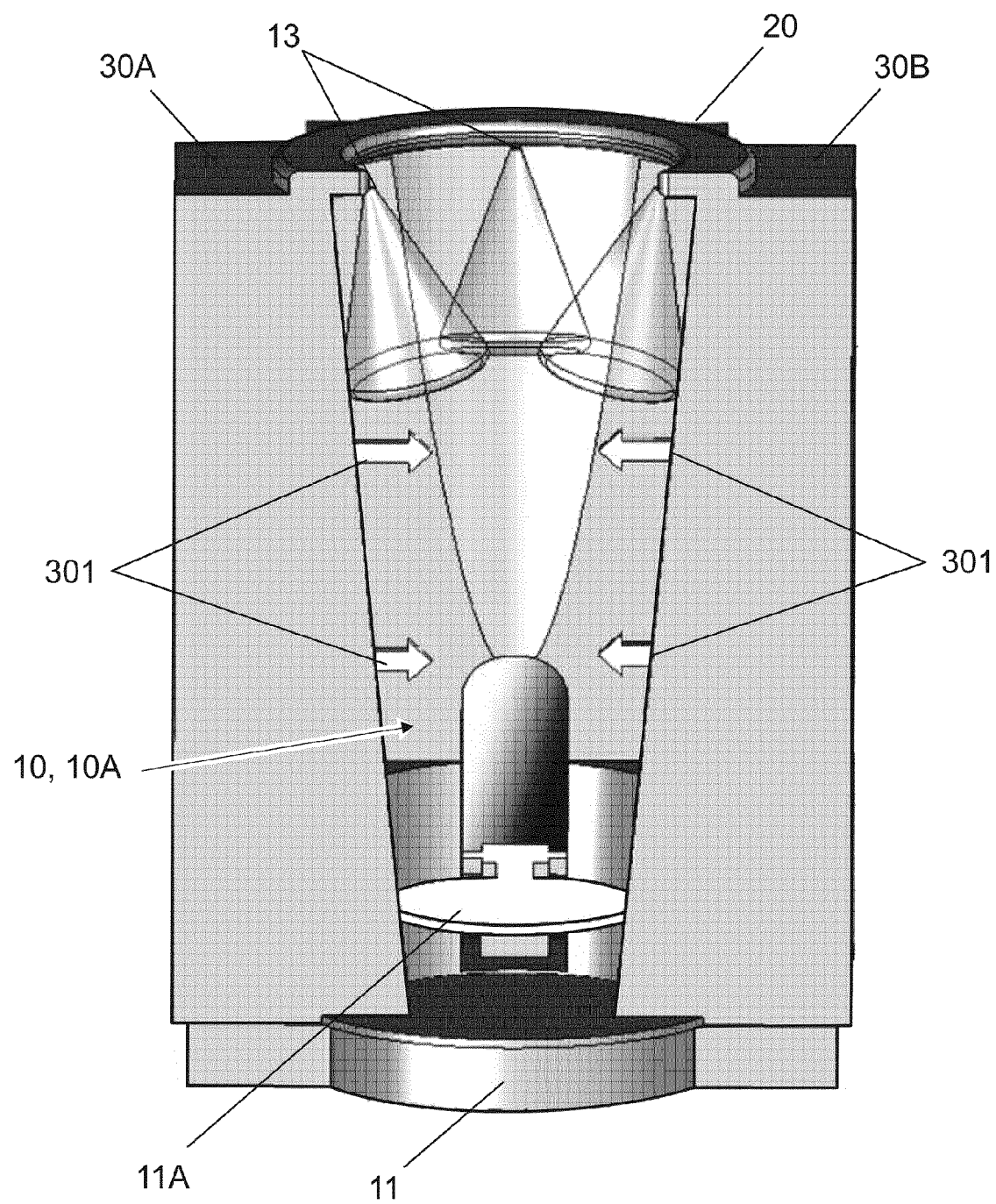

FIGS. 1, 2A and 2B illustrate exemplary configurations for a cryocabin arrangement 100 for implementing an operating method, according to the embodiments.

Figure 3A:
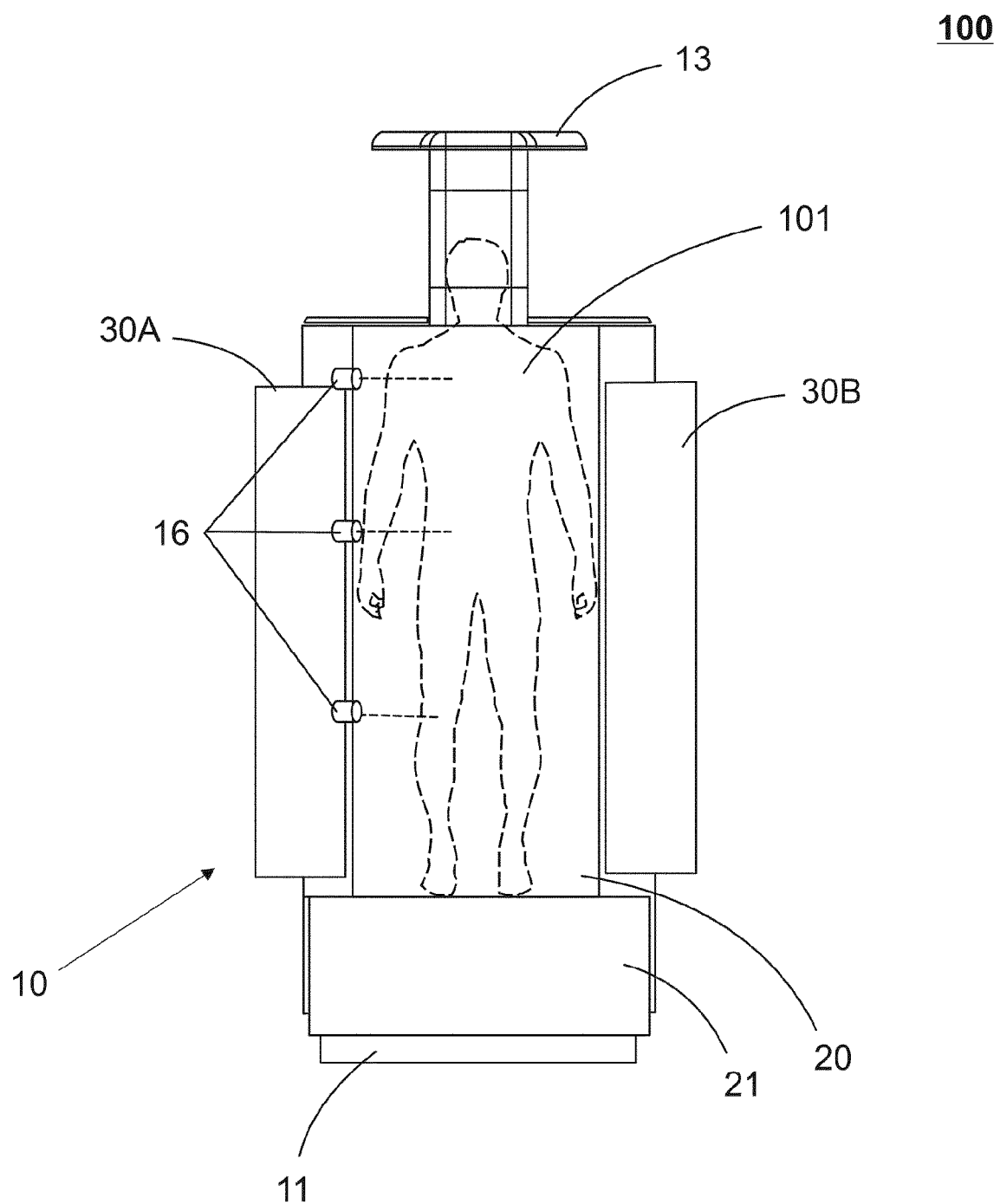
FIG. 3A schematically illustrates the cryocabin arrangement 100, viewed from the rear, with a user accommodated in the cabin.
Figure 3B:
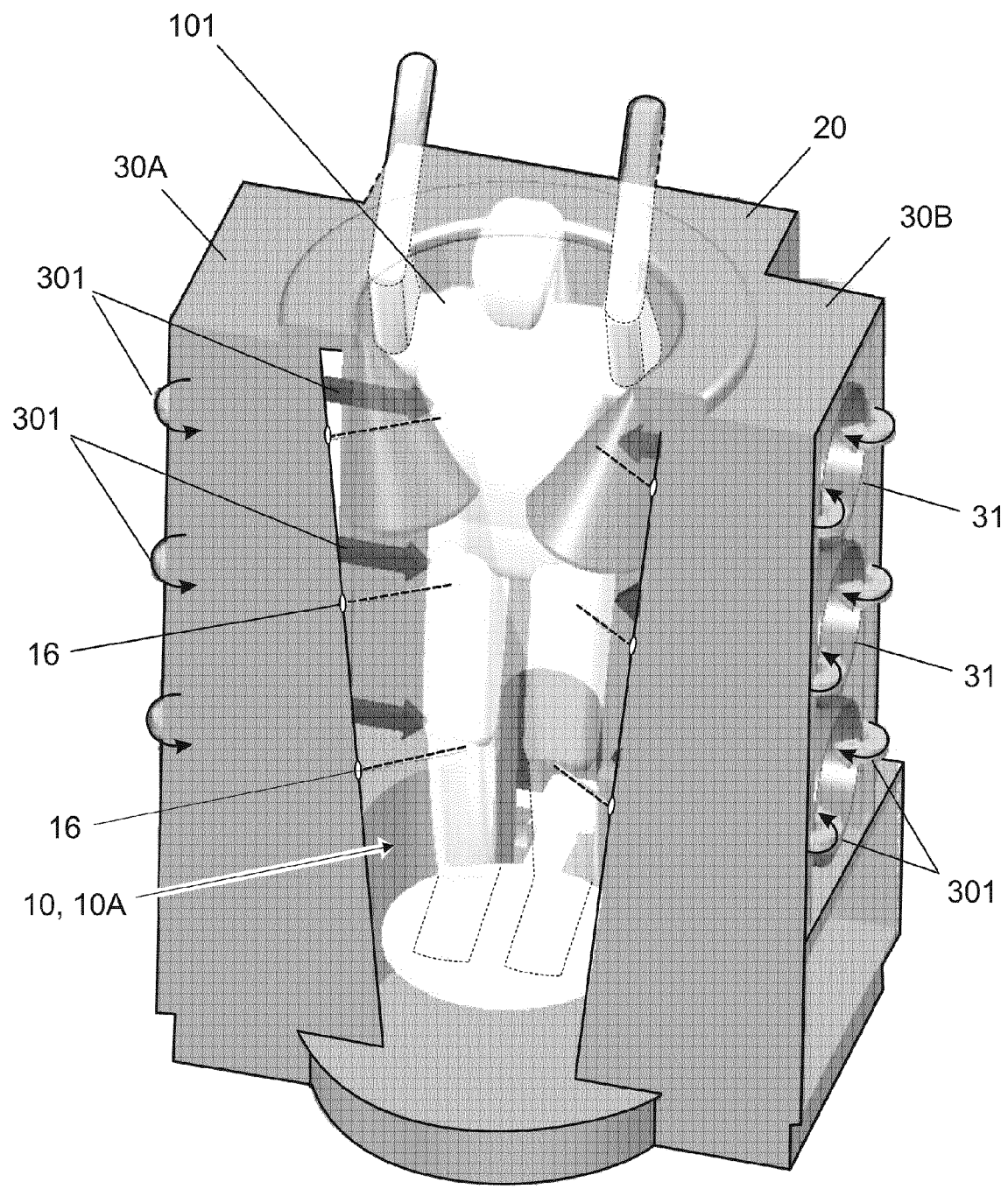
FIG. 3B is a prospective view of the cryocabin arrangement 100 with a user accommodated in the cabin.

The arrangement 100 comprises a cabin 10 and a cooling unit 20. The cabin 10 is configured as an open-top chamber with an interior 10A suitable for accommodating a user. In presented configurations, the cabin 10 is configured as a vertical open-top chamber suitable for accommodating a standing adult human in a manner shown on FIGS. 3A and 3B.

It should be noted that upon appropriate modifications, the cabin 10 can accommodate a standing nonhuman mammal. In particular, the cabin can be modified to accommodate a so called companion animal or a pet, such as a canine, an equine, and the like.

The cabin further comprises a base 11 and a door 12, the latter being implemented as a hinged door or as a sliding door. The base 11 can be further equipped with a standing platform 11A or a similar appliance configured to move up and down along a vertical axis, whereby the cabin interior can be adapted to the height of the user. Position of the user in the cabin is adjusted, by means of said standing platform 11A, such that the upper edge of the cabin is approximately at a neck level of the user, whereby head remains above the open-top upper edge (viz. outside the cabin).

The cabin comprises a number of illumination devices 13 configured as spot light sources located along the upper edge of the cabin (FIGS. 2A, 2B) optionally combined with a central light source as shown on FIG. 1. Location and the number of illumination sources can vary depending on particular cabin design.

The cabin can further comprise a number of parameters displays 14 (FIG. 1), to display a variety of treatment related parameters, such as time, ambient temperature, pressure, humidity, and the like. The parameter screen(s) 14 can be further configured to show user-related parameters, such as real-time readouts from a thermographic camera, for example.

The cabin 10 is thermally insulated. In some instances, a number of protection shields 17 is positioned against the cooling unit 20 and the fluid circulation units 30 to protect the user from coolant streams produced thereby (FIG. 2A). The interior of the cabin 10 including protection shields 17 may be padded by a suitable cold-resisting material. The shields 17 can be configured as temporary, easily dismountable appliances.

The cooling unit 20 comprises blowing appliances, such as blower(s) or impeller(s), for example, to deliver cooling fluid 201 directly into the cabin 10 (FIG. 1). The cooling unit 20 is preferably provided as a vertically standing unit that delivers cooling fluid 201 into the cabin 10 essentially along the entire height of said cabin. Intake fluid, preferably gaseous medium, such as air (e.g. ambient air), pressurized and optionally pre-cooled in a compressor 21, is guided into the cooling unit comprising at least one heat-exchanger (not shown).

The cooling unit 20 produces a stream or streams of cooling fluid 201 entering the cabin at a substantially low speed, within a range of 0.2-5 meters per second (m/s).

The arrangement 100 further comprises a number of fluid circulation units 30, which intake and (re)circulate the cooling fluid 201 delivered into the cabin 10, and return recirculated cooling fluid, in the form of return fluidic streams 301, back into the cabin. For the sake of clarity we note that cooling fluid indicated by reference numbers 201, 301 is the same substance (e.g. air) having essentially identical temperature. Provision of diverse reference numbers (201, 301) aims at distinguishing between the cooling fluid streams 201 entering the cabin directly from the cooling unit 20 and the cooling fluid streams 301 recirculated in the circulation units 30 and thus re-entering the cabin 10.

The cooling fluid 201, 301 distributed inside the cabin 10 is adjusted to a temperature t2 equal to or above −40 degrees Celsius (° C.) (FIG. 1A). In embodiments, temperature of said cooling fluid 201, 301 is provided within a range of −45° C. to −15° C., preferably, within a range of −35° C. to −25° C. In non-limiting examples, the cooling fluid 201, 301 is adjusted to temperatures t2 of −28° C., −29° C. or −30° C.

At these values attaining the cold-induced thermal shock at skin surface and the underlying tissue can be the most straightforward.

Figure 4:
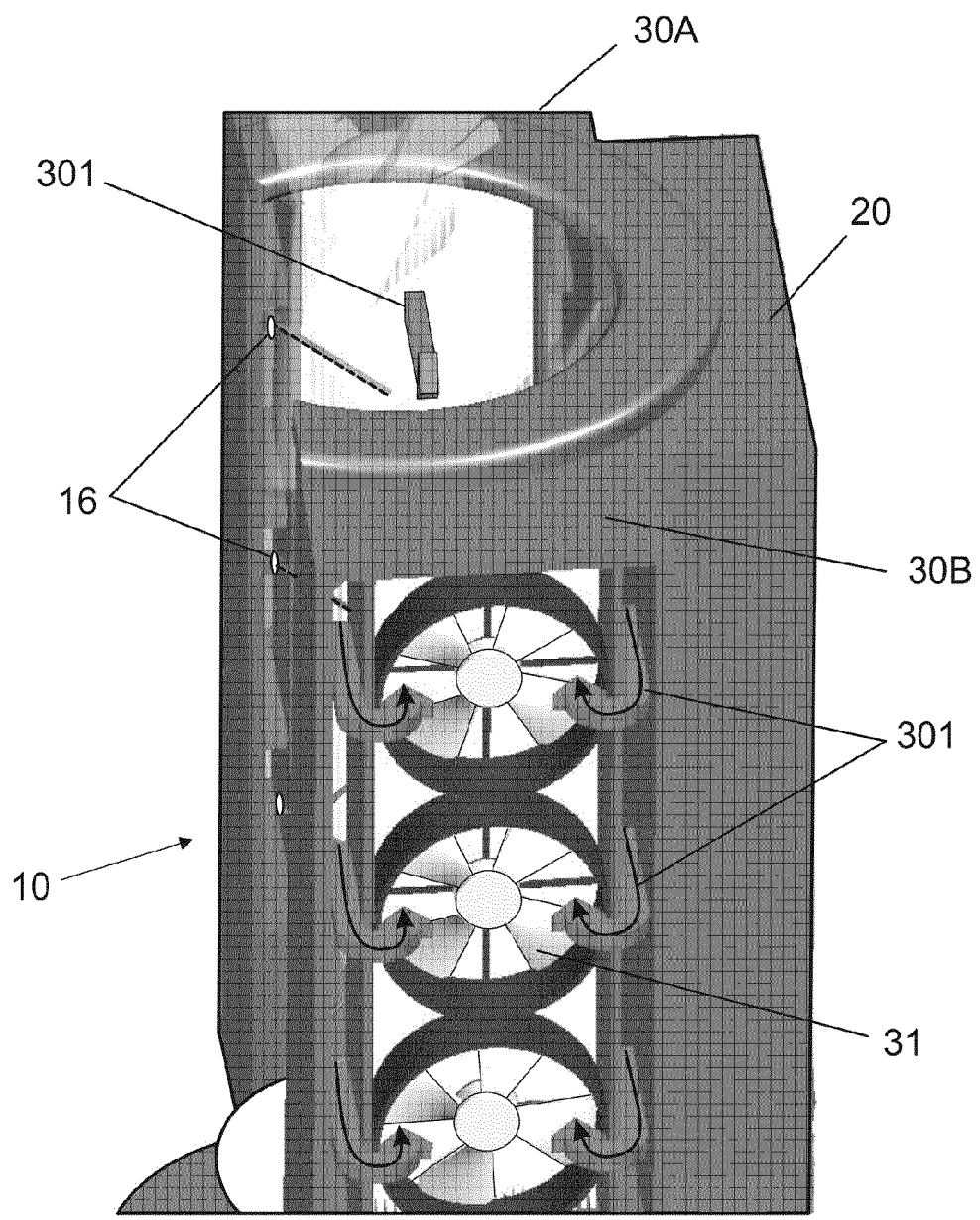
FIG. 4 shows an exemplary implementation for a fluid circulation unit provided in the cryocabin arrangement 100.

In preferred configurations the arrangement 100 comprises two fluid circulation units 30A, 30B arranged at both sides of the cooling unit 20 essentially opposite one another (FIGS. 2A, 2B). Each fluid circulation unit 30 preferably comprises a number of impeller devices 31 (see FIG. 4) for fluid recirculation.

The cabin arrangement 100 is preferably electrically operated. The arrangement thus comprises at least one electric motor (not shown) positioned such that heat produced thereby does not affect the cabin 10, or any one of the cooling- or fluid circulations units 20, 30, accordingly. The impeller devices 33 can be driven by electric power produced by said electric motor.

Figure 5:
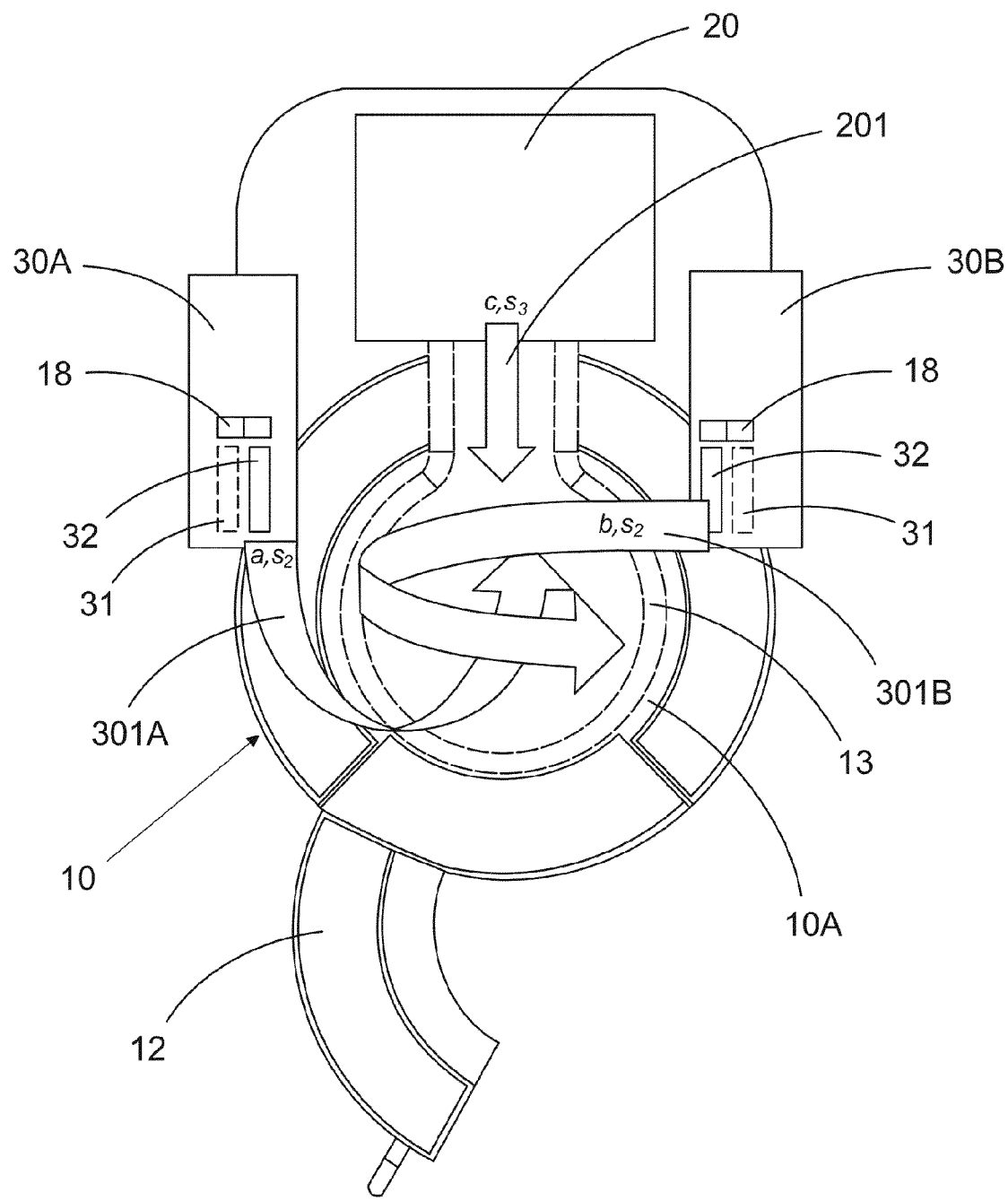
FIG. 5 schematically illustrates the cryocabin arrangement 100, viewed from the top with fluidic streams established in a cabin.

In some configurations, each circulation unit 30 comprises a number of cooling fluid intake appliances 31 configured to intake, by suction, for example, fluid streams 201 from the cabin and a number of cooling fluid return appliances 32 configured to return recirculated fluid streams 301 back into the cabin (FIGS. 1 and 5). The intake appliances can be configured as suction nozzles, for example, whereas the return appliances can be configured as any kind of nozzles or spouts suitable for directing fluids into a predetermined direction. In embodiments, the return appliances 32 are provided as inclined nozzles configured to return recirculated cooling fluid 301 into the cabin 10 along a path inclined at an angle within a range of 30-50 degree related to vertical walls of said cabin. In some configurations, said inclination angle constitutes 45 degrees in any one of upward and downward directions. The return nozzles can be configured as automatically adjustable rotating nozzles (e.g. ball-type nozzles), that enable adjusting jet direction of such nozzle within a range of 0-50 degree.

The intake appliances 31 and, in particular, return appliances 32 are advantageously disposed along the entire height of the cabin such, as to target all body regions, such as the upper body/chest region, waist region, the lower body and the legs.

Fluid circulation units 30 produce a stream or streams of cooling fluid 301 (re)entering the cabin at a substantially high speed, within a range of 15-25 meters per second (m/s). However, each return appliance 32 can be configured to produce a fluidic jet of a variable speed or flow velocity.

In an exemplary operating cycle, the cooling unit 20 is configured to produce fluidic streams 201 that enter the cabin at a speed of about 2 m/s; whereas the fluid circulation units 30 are configured to produce fluidic streams 301 that (re)enter the cabin at a speed of about 18 m/s.

Control over cooling fluid distribution via the return appliances 32 can be implemented locally by means of control devices 18 (FIG. 5). Control device(s) 18, such as relays, valves (e.g. solenoid valves), related actuators and other devices are used to control cooling fluid distribution variables, such as at least speed (s1, s2) and direction (a, b) based on an input received into a central processing unit 41, as described herein below. The control device 18 can be configured to control an individual return appliance 32 or a number of appliances 32.

The cabin arrangement 100 further comprises a plurality of sensor devices 16 (FIGS. 3A, 3B), preferably disposed in the interior 10A of the cabin. The sensor devices 16 are disposed at different heights along the internal perimeter of the cabin (on internal walls and, optionally, on an inner side of the door) to obtain measurements uniformly across the entire interior 10A. The sensor devices 16 are preferably configured as thermal sensors/transmitters that measure temperature (t1) at skin surface of the user and/or temperature (t2) in the cabin throughout the operation cycle and send measurement data to the processing unit 41 (FIGS. 1B, 5). Optionally, some sensor devices can be configured to measure additional variables, such as pressure, humidity, presence of chemical substances in the ambient, and the like.

Thermal sensor devices that measure temperature (t1) at the user skin surface can be configured as infrared (IR) sensors, for example. Still, any other sensor device capable of measuring temperature and/or detecting heat emitted from skin surface of the user positioned in the cabin 10 can be utilized.

In some configurations, a number of thermographic cameras, comprising an at least one thermal sensor device 16, as described above, can be integrated in the interior of the cabin 10. Said thermographic camera(s) and/or the individual sensor devices 16 can be configured to generate a thermal map based on temperature variables t1 measured at the user skin surface.

User-specific measurement data obtainable by said sensor devices 16 during the operating cycle forms at least a part of the input data received by the processing unit 41. In said processing unit the measurement data is analyzed and an output is generated in the form of signals sent to the units 20 and 30 for adjusting, to a predetermined level, distribution of the cooling fluid 201, 301 in the cabin 10 during the operation cycle. Adjustable fluidic flow distribution variables include at least source, velocity, speed and/or direction of a fluidic flow conveyed into the cabin 10 from the cooling unit 20 and/or the fluid circulation units 30.

Other ("external") input data can be obtained prior to beginning of the operating cycle. Such data is also user-specific and comprises information about the user, such as height, weight, age, gender, and the like. During data processing, said external user-specific data can be optionally combined with the measurement data obtained from the sensor devices 16.

Obtaining measurement (input) data from the sensor devices 16, processing said data and producing an output (a series of commands to select a source, such as a nozzle or nozzles 32 and/or to render fluidic streams 201, 301 with a predetermined speed and/or direction) is conducted in real time continuously during the operation cycle. By means of the local control devices 18, the return appliances 32, such as nozzles, can be selectively set open/closed or rotated into a predetermined direction The processing unit 41 can be integrated within the cabin arrangement 100 or provided as a standalone solution, e.g. as a local- or remote computer system, for example, including, but not limited to PC, portable or tablet computer, mobile phone, smart phone, PDA and the like. To encompass either option the reference number 41 is shown on FIG. 1A in parenthesis.

The computer system may be further configured to display measurement parameters obtainable from the sensor devices 16, for example, in the form of visualizations (e.g. thermographic images/thermal maps in 2D and/or 3D). These visualizations, generally available to the operator of the system 100, can be further synchronized with images visible to the user via the parameter displays(s) 14, for example. The computer system may, for example, present temperature variables (t1, t2) measurable with regard to different body regions during the operating cycle as a three-dimensional interactive visualization.

The cabin arrangement further comprises a control terminal 42 (FIG. 1) equipped with a user interface, preferably, a graphical user interface. The latter can be realized in the form of a display screen, such as a touchscreen, for example. User interface may also comprise an at least one audio input-output device and an associated circuitry. FIG. 1 shows provision of the control terminal 42 integrated into the cabin 10, such as into the door 12 or a sidewall of the cabin. The control terminal 42 can be connected, in wired or wireless manner, to the processing unit 41.

The control terminal 42 is further provided with one or more processing devices containing a processing circuitry capable of interpreting and executing instructions input via the user interface, said processing devices being realized as microprocessors, microcontrollers, digital signal processors, programmable logic chips etc.

The control terminal 42 can be configured to acquire a direct electrical communication with each of the control devices 18 regulating distribution of recirculated cooling fluid 301 into the cabin 10 and/or with a number of regulating valves provided within the cooling unit 20 and the fluid circulation unit(s) 30.

In some instances, the spot-light devices 13 (FIGS. 2A, 2B, the upper edge of the cabin) can be configured to emit light within a predetermined portion of the electromagnetic spectrum, preferably, within the visible spectrum, defined as the wavelength range of electromagnetic radiation between 380 and 750 nanometers (nm). In some instances, each device 13 can be configured to emit light at a single fixed wavelength, such as blue (about 490 nm to about 450 nm), green (about 560 nm to about 520 nm) and/or red (about 620 nm to about 750 nm). In such an event, the illumination devices 13 can be advantageously provided as Light Emitting Devices (LEDs) or any other devices appropriate for use, in particular, in view of development of the technology.

In some instances, combining light sources configured to emit light at different wavelengths into arrays is advantageous due to ability of light emitted at various wavelengths to target particular dermal conditions. Thus, blue light is known to effectively treat a variety of dermal infections, such as acne and related skin inflammations. Green light is, in turn, known to targets dark circles, pigmentation, and the like. Additionally, green light calms irritated skin and it is often used in the anti-age treatments. Red light accelerates blood circulation at skin surface and increases collagen production, which is essential for various skin stimulation- and rejuvenation (cosmetic) treatments.

A method 500 for operating the cryocabin arrangement 100 is schematically represented on FIG. 1B. In embodiments, the method 500 is a computer-implemented method. In the method, the user-specific data is received, at 501, into the processing unit 41. The user-specific data received at 501 comprises indications measurable at skin surface of the user upon delivery of cooling fluid 201 into the cabin 10 via the cooling unit 20 followed by intake and recirculation of said cooling fluid by fluid circulation units 30, which further return recirculated cooling fluid 301 inside said cabin.

The user-specific data received at 501 comprises at least temperature indications obtainable from a number of sensor devices 16. Said user-specific data can comprise information on heat extraction detected and/or measured at the skin surface of the user positioned into the cabin 10.

At 502, the user-specific data is processed in the processing unit 41.

The method continues at 503 (generation of the output), wherein, based on said user-specific data, distribution of said cooling fluid 201, 301 inside the cabin 10, is selectively adjusted in terms of at least speed and/or direction of a fluidic flow, to a predetermined level a during an operation cycle. Adjustable variables include at least flow speed s1, s2, s3 and/or flow direction vectors a, b, c. A predetermined number of return appliances 32 can further be selected for directing streams 201 and/or 301 into the cabin.

In embodiment, the method comprises adjusting distribution of recirculated cooling fluid 301 returned into the cabin via the return appliances 32 (fluid circulation unit(s) 30) optionally controlled by the control devices 18 (adjusting speed variables s1, s2 and direction variables a, b). In another embodiment, fluid flow variables, such as at least speed s3 and/or direction vector(s) c, can be adjusted also for the stream(s) 201 conveyed into the cabin from the cooling unit 20. The latter configuration is optional and it is indicated on FIG. 1B by dashed lines.

In embodiments, the data received from the thermal sensor devices 16 concerns the temperature indications measurable at the user skin surface (variable t1; FIG. 1B). It is particularly advantageous that the sensor devices 16 are configured to detect a particular region or regions on skin surface at which temperature has reached or about to reach the values within a range of −1 to 0 degrees Celsius, to register and to transmit these indications to the processing unit 41. In the method, the cooling fluid distribution related variables, such as at least flow speed and/or direction vectors are further adjusted to values, at which the temperature at skin surface can be reached and maintained at a level within a range of −1 to 0° C. during the operating cycle.

By adjusting fluidic flow 201, 301 distribution parameters during the operation cycle, as disclosed hereinabove, a controlled cold impact can be applied onto the entire body of the user (excluding head), whereby the temperature at skin surface across the entire body area can be decreased to reach values (t1) within −1 to 0 degrees Celsius. By regulating fluidic flow related parameters, such as at least speed, direction and/or source, based on the data produced by the thermal sensor devices 16, these temperature values can be reached nearly simultaneously throughout the entire body of the user (viz. for the body areas having high-, moderate- and low perception threshold for cold impact).

The temperature values within a range of −1 to 0° C. can be considered as a threshold, thereafter the fluid distribution variables should be maintained essentially stable. Thus, the temperature at skin surface should preferably be no lower than approximately −1° C. and no higher than approximately 0° C. During the operating cycle, fluid distribution variables (speed, direction vectors, etc.) are adjusted to and maintained at a level sufficient to reach and maintain the temperature variable(s) t1 measureable at the user skin surface, within a range of −1 to 0° C. Duration of each operating cycle is determined individually.

Temperature at skin surface slightly below zero or equal to zero (° C.) is sufficient to develop the cold-induced thermal shock response (cold shock response) in skin and the underlying tissue, such as subcutaneous tissue. It has been observed that the temperature variable t1 measurable at the skin surface reaches the values between −1 to 0° C., when the temperature regime t2 inside the cabin is within −28° C. to −30° C., and the speed s1, s2 of fluidic stream(s) 301 is within a range of 15-20 m/s, in some instances, approximately 18 m/s. Based on the measurements obtainable from the thermal sensor devices 16 in real time, direction vectors a, b for the fluidic streams 301A, 301B, accordingly, produced by the return appliances 32 can be adjusted (FIG. 5).

In some instances, the fluid distribution variables can be adjusted such, as to create vortical (vortex) flow essentially around a central vertical axis of the cabin.

For clarity purposes the expression "cold-induced thermal shock response" is utilized in the present disclosure with reference to the processes occurring in skin and the underlying tissue during and instantly after the controlled cold impact, which processes include, but are not limited to: vasomotor response, such as cold-induced alteration of the diameter in peripheral blood vessels (hereby, narrowing or vasoconstriction and subsequent widening or vasodilatation) leading to acceleration and intensification of blood circulation and increased oxygen supply to blood and tissues; and release into bloodstream of the neuromediator substances, such as noradrenaline, serotonin and endorphins, for example. Amongst aforesaid, noradrenaline in known for its involvement in reducing inflammation processes; whereas serotonin and endorphins are often referred to as natural painkillers.

The invention takes into account a so called "wind chill factor" principle (whereby the body feels far colder than the ambient temperature due to the "wind", viz. flow of cold air) attainable by directing cooling fluid inside the cabin at a predetermined speed and in predetermined direction, whereby a high-speed flow is established essentially along the entire height of the cabin.

In some configurations, the cabin arrangement 100 further comprises a number of vaporizer devices 15 configured to deliver into the cabin an aqueous-based solution 15A (FIG. 1) prior to or during the operation cycle. The vaporizer devices are preferably configured as spray vaporizers, jet-vaporizers, or atomizers. The solution 15A is supplied into the cabin from a number of replaceable containers (not shown) disposed outside the cabin.

Accordingly, the method for operating the cryocabin arrangement 100 can be further optionally supplemented by delivery of an aqueous-based solution 15A, preferably by spraying, into the cabin 10 via a number of said vaporizer devices 15.

To further promote heat extraction from skin, the solution 15A can be delivered into the cabin 10 prior to or during the operating cycle. Delivery of the solution 15A before the beginning of the operating cycle is advantageous. It has been observed that using micellar aqueous solutions combined with vegetable oils allows increasing heat extraction from skin surface almost twice, as compared to plain water. Delivery of the solution 15A into the cabin serves complementary purposes; therefore, the step involving delivery of said solution into the cabin can be omitted.

The aqueous-based solution 15A comprises an aqueous component and an oil component. The oil component is preferably a vegetable oil selected, in a non-limiting manner, from the group consisting of: argan oil, sunflower seed oil, olive oil, jojoba oil, avocado oil, almond oil, coconut oil, castor oil, rosehip oil, and any combination thereof. This list should not be treated as exhaustive, as any other vegetable (plant-derived) oil having an established use is cosmetics, for example, can be utilized in the solution 15A.

In mentioned solution 15A, the aqueous component is water, more preferably, a micellar aqueous solution commonly referred to as micellar water.

Micellar aqueous solutions are dispersions of micelles in aqueous media, typically water. Micelles are spherical formations of surfactants having hydrophilic heads facing the aqueous medium and hydrophobic tails inside the sphere. Micellar aqueous solutions are common water-based skin cleansers that do not have to be rinsed off afterwards. An idea behind using micellar solutions as cleansers is that micelles are attracted to oil and dirt so that they can remove these impurities from skin. Typically, micellar cleansers are used as all-in-one cleansers and are especially beneficial for individuals with sensitive skin.

A composition for use in a method for operating the cryocabin arrangement 100, according to the embodiments, is provided in the form of an aqueous-based solution 15A and comprising an aqueous component and an oil component, wherein the aqueous component is a micellar aqueous solution and wherein the oil component is a vegetable oil selected from the group consisting of: argan oil, sunflower seed oil, olive oil, jojoba oil, avocado oil, almond oil, coconut oil, castor oil, rosehip oil, and any combination thereof.

In a non-limiting example, the composition 15A comprises a micellar aqueous solution, sunflower seed oil, glycerin and at least one surfactant. The surfactants include, but are not limited to hexylene glycol, disodium cocoamphodiacetate (DSCADA), disodium EDTA and any combination thereof. The composition can further comprise preservatives and/or antibacterial compounds, such as myrtrimonium bromide, for example. The composition can further employ purified water (e.g. reverse osmosis purified water) as a solvent. The composition can further include additional compounds, such as poloxamers (polymers with water-tension reducing and antibacterial properties), a variety of vitamins, aromatizes and other skin-care components. Preferred pH range for the solution 15A is within 5.0 -7.0, exemplary pH values include 5.0, 5.5, 6.0, 6.5 and 7.0.

It shall be appreciated by those skilled in the art that the embodiments set forth in the present disclosure may be adapted and combined as desired. The disclosure is thus intended to encompass any possible modifications of the cryocabin arrangement, recognizable by those of ordinary skill in the art, within a scope of appended claims.

The invention claimed is:

1. A method for operating a cryocabin arrangement (100) that is equipped with an open-top cabin (10), a cooling unit (20), and a plurality of fluid circulation units (30), the method comprising:
    receiving user-specific data comprising at least temperature indications (t1), measureable: by a plurality of sensor devices (16), at a skin surface of a user upon delivery of cooling fluid (201) into the cabin (10) via the cooling unit (20), followed by intake and recirculation of said cooling fluid by fluid circulation units (30) which also return recirculated cooling fluid (301) inside said cabin; and
    based on said user-specific data, selectively adjusting, during an operation cycle, a plurality of variables related to a distribution of said cooling fluid (201, 301) inside the cabin to a predetermined level, said variables comprising at least one of a speed and a direction of a fluidic flow,
    wherein the cooling fluid (201, 301) distributed inside the cabin (10) is adjusted to a temperature (t2) within a range of −45° C. to −15° C.

2. The method of claim 1, wherein the fluid distribution variables are adjusted so that said temperature indications (t1) measureable at the skin surface of the user are within a range of 0° C. to −1° C.

3. The method of claim 2, wherein the steps of receiving the user-specific data and selectively adjusting the distribution of the cooling fluid (201, 301) inside the cabin (10) are performed in real-time.

4. The method of claim 2, wherein the cooling fluid is air.

5. The method of claim 2, wherein the cooling fluid (201) is delivered into the cabin (10) along an entire height of said cabin.

6. The method of claim 2, wherein recirculation and return of the cooling fluid into the cabin is implemented by the fluid circulation units (30) arranged at opposing sides of the cooling unit (20).

7. The method of claim 1, wherein the steps of receiving the user-specific data and selectively adjusting the distribution of the cooling fluid (201, 301) inside the cabin (10) are performed in real-time.

8. The method of claim 7, wherein the cooling fluid is air.

9. The method of claim 7, wherein the cooling fluid (201) is delivered into the cabin (10) along an entire height of said cabin.

10. The method of claim 1, wherein the cooling fluid is air.

11. The method of claim 10, wherein the cooling fluid (201) is delivered into the cabin (10) along an entire height of said cabin.

12. The method of claim 1, wherein the cooling fluid (201) is delivered into the cabin (10) along an entire height of said cabin.

13. The method of claim 1, wherein recirculation and return of the cooling fluid into the cabin is implemented by the fluid circulation units (30) arranged at opposing sides of the cooling unit (20).

14. The method of claim 1, wherein recirculated cooling fluid (301) is returned into the cabin (10) along a path inclined at an angle within a range of 30-50 degrees with respect to vertical walls of said cabin.

15. The method of claim 1, wherein the cryocabin arrangement (100) is electrically operated.

16. The method of claim 1, wherein the distribution of the cooling fluid (201, 301) inside the cabin is supplemented by delivery of an aqueous-based solution (15A) into the cabin (10) by way of vaporizer devices (15).

17. The method of claim 16, wherein the aqueous-based solution (15A) comprises an aqueous component and an oil component.

18. The method of claim 17,
wherein the oil component is a vegetable oil selected from the group consisting of: argan oil, sunflower seed oil, olive oil, jojoba oil, avocado oil, almond oil, coconut oil, castor oil, rosehip oil, and any combination thereof, and
wherein the aqueous component comprises a micellar aqueous solution.

19. An electrically operated cryocabin arrangement (100), comprising:
an open-top cabin (10);
a cooling unit (20) configured to deliver cooling fluid (201) directly into the cabin (10);
a plurality of fluid circulation units (30);
a data processing unit (41) configured to
receive user-specific data comprising at least temperature indications (t1), measureable at a skin surface of the user by a plurality of sensor devices (16) upon delivery of cooling fluid (201) into the cabin (10) via the cooling unit (20), followed by intake and recirculation of said cooling fluid by fluid circulation units (30) which also return recirculated cooling fluid (301) inside said cabin, and
based on said user-specific data, selectively adjust, in real time, a distribution of said cooling fluid (201, 301) inside the cabin (10), in terms of at least one of a speed and a direction of a fluidic flow, to a predetermined level during an operation cycle,
wherein a plurality of fluid distribution variables related to the distribution of said cooling fluid are adjusted so that the temperature indications (t1) measureable at the skin surface of the user are within a range of 0° C. to −1° C., and
wherein the cooling fluid (201, 301) distributed inside the cabin (10) is adjusted to a temperature (t2) within a range of −45° C. to −15° C.

20. The cryocabin arrangement (100) of claim 19, further comprising:
vaporizer devices (15) configured to deliver an aqueous-based solution (15A) into the cabin (10).

* * * * *